(12) United States Patent
Guignet

(10) Patent No.: US 12,241,892 B2
(45) Date of Patent: Mar. 4, 2025

(54) IN SITU SERIAL DILUTION METHOD

(71) Applicant: BIO-RAD EUROPE GMBH, Basel (CH)

(72) Inventor: Emmanuel Guignet, Cressier FR (CH)

(73) Assignee: BIO-RAD EUROPE GMBH, Basel (CH)

( * ) Notice: Subject to any disclaimer, the term of this patent is extended or adjusted under 35 U.S.C. 154(b) by 1468 days.

(21) Appl. No.: 16/626,584

(22) PCT Filed: Jun. 22, 2018

(86) PCT No.: PCT/IB2018/000768
§ 371 (c)(1),
(2) Date: Dec. 26, 2019

(87) PCT Pub. No.: WO2019/002935
PCT Pub. Date: Jan. 3, 2019

(65) Prior Publication Data
US 2020/0116710 A1    Apr. 16, 2020

Related U.S. Application Data

(60) Provisional application No. 62/524,832, filed on Jun. 26, 2017.

(51) Int. Cl.
*G01N 33/543* (2006.01)

(52) U.S. Cl.
CPC .............. *G01N 33/54306* (2013.01)

(58) Field of Classification Search
CPC ............ B01L 3/5085; G01N 33/555; G01N 33/559; G01N 33/537; G01N 33/538; G01N 33/539; G01N 33/541; G01N 33/5094; G01N 33/54306
USPC .... 422/415, 68.1, 548, 549, 554; 435/288.4; 436/515, 520, 538, 539, 540, 541; 530/413
See application file for complete search history.

(56) References Cited

U.S. PATENT DOCUMENTS

| | | |
|---|---|---|
| 4,305,721 A | 12/1981 | Bernstein |
| 5,460,940 A | 10/1995 | Yves et al. |
| 5,650,068 A | 7/1997 | Chachowski et al. |
| 6,114,179 A | 9/2000 | Lapierre et al. |
| 8,187,538 B2 | 5/2012 | Jakubowicz et al. |
| 8,496,878 B2 | 7/2013 | Jakubowicz et al. |
| 10,509,028 B2 | 12/2019 | Agusti et al. |
| 2011/0159477 A1 | 6/2011 | Nilsson et al. |

(Continued)

FOREIGN PATENT DOCUMENTS

| | | |
|---|---|---|
| AU | 2001258469 B2 | 11/2001 |
| CN | 101021540 | 8/2007 |
| CN | 103547921 A | 1/2014 |

(Continued)

OTHER PUBLICATIONS

Written Opinion in International Application No. PCT/IB2018/000768, Oct. 30, 2018, pp. 1-7.

(Continued)

*Primary Examiner* — Christopher L Chin
(74) *Attorney, Agent, or Firm* — SALIWANCHIK, LLOYD & EISENSCHENK

(57) ABSTRACT

Provided herein are methods of determining a concentration of an analyte in a sample using in situ serial dilution.

20 Claims, 13 Drawing Sheets

(56) References Cited

U.S. PATENT DOCUMENTS

2012/0282635 A1  11/2012  Wardlaw et al.
2014/0141995 A1  5/2014  Crisanti et al.

FOREIGN PATENT DOCUMENTS

| EP | 2 515 271 A1 | 10/2012 | |
|---|---|---|---|
| JP | 2011-512524 | 4/2011 | |
| RU | 2526820 C1 * | 4/2013 | ............. G01N 33/53 |
| WO | WO 99/50673 | 10/1999 | |
| WO | WO 03/044217 A2 | 5/2003 | |
| WO | WO 2005/064347 | 7/2005 | |
| WO | WO 2009/097188 | 8/2009 | |
| WO | WO 2016/184924 | 11/2016 | |

OTHER PUBLICATIONS

Scabet. "Precision of Antibody Titration in Gel versus Tube," AABB Future Leader Scholarship Awards, Published May 21, 2013; 13 pages. https://www.aabb.org/development/scholarships/Documents/12scabet.pdf.

Bromilow, I.. DiaMed-ID Micro Typing System "Good Laboratory Practice Titration procedures," Copyrighted 1999, downloaded Jun. 2, 2017, 8 pages.

American Proficiency Institute—2012 1st Test Event "Educational Commentary—Antibody Titrations," Copyrighted 2012 by American Society of Clinical Pathology, URL: http://www.api-pt.com/Reference/Commentary/2012Abbank.pdf, downloaded Apr. 17, 2017, 5 pages.

Novaretti et al. "Comparison of conventional tube test with diamed gel microcolumn assay for anti-D titration," Clin. Lab. Haem., 2003, vol. 25, pp. 311-315.

Insert—"Blood Grouping Reagent DG Gel 8 ABO/Rh + Kell REF 210383 3034946 Instructions for Use." (2013) Distributed by Novartis Vaccines and Diagnostics, Inc, https://www.fda.gov/media/86207/download, downloaded Apr. 6, 2017, 8 pages.

Powell, V., "Blood Group Antigens and Antibodies" NYU Langone Medical Center, PowerPoint slides, Apr. 18, 2017, 69 pages.

"MLAB 2461 Clinical II Immunohematology Activity 11 MTS Gel Testing" Austin Community College course: MLAB 2461 Clinical—Clinical/Medical Laboratory Technician II. Web Author: Terry Kotrla, Original publication date: Jan. 2008, 5 pages.

Endoh, T. et al. "Prewarm Technique Reduces the Detection Efficiency For Rh System Antibodies" *Japanese Journal of Transfusion Medicine,* 2005, pp. 327-332, vol. 51, No. 3.

* cited by examiner

IN SITU SERIAL DILUTION METHOD

CROSS-REFERENCE TO RELATED APPLICATIONS

This application is the U.S. national stage application of International Patent Application No. PCT/IB2018/000768, filed Jun. 22, 2018, which claims the benefit of U.S. Provisional Patent Application No. 62/524,832, filed Jun. 26, 2017.

BACKGROUND

In blood banking, when a clinically significant antibody capable of causing hemolytic disease of the newborn or fetus is detected in a pregnant woman, the antibody titer (or semi-quantitative concentration) is determined by performing an antibody titration. Throughout pregnancy, the mother's antibody titer is repeated to determine if there is a rise in titer or concentration of the antibody. A rise in antibody titer by three or more dilutions is considered clinically significant and suggests that the fetal red blood cells (RBCs) possess the antigen to the corresponding antibody. Once the titer reaches a critical threshold and the fetus is at least eighteen weeks gestational age, additional studies, such as ultrasound, Doppler sonography, amniocentesis, or cordiocentesis, will be performed. These procedures monitor the level of anemia in the fetus and indicate the necessity of intrauterine transfusion or other interventions.

Antibody titration is also clinically indicated in separating multiple antibodies, antibody identification, and performing ABO isohemagglutinin titers on apheresis donor platelet units or organs that are to be transplanted across ABO boundaries. Antibody titration may also be undertaken to (i) assess the antigen site density of red cell reagents, (ii) assess the characteristics of a new antiserum or compare a new batch with a previous one, (iii) investigate so-called High Titer Low Avidity (HTLA) antibodies (for example antibodies known to belong to the Knops blood group system), (iv) determine the relative specificity of autoantibodies in Warm Antibody Immune Hemolytic Anemia (WAIHA), (v) perform studies on the saliva from secretors of soluble blood group substance, (vi) determine the antigen status of direct antiglobulin test (DAT) positive cells when reagents are unavailable or unsuccessful in removing IgG from the cells to be types and (vii) determine the titre, specificity and thermal amplitude of a cold autoantibody, for example, anti-I.

Antibodies are usually titrated by making serial, two-fold dilutions of the patient's plasma and grading the strength of reactivity with selected red blood cells (RBCs) that possess the corresponding antigen. The results of a titer are reported as the reciprocal of the highest dilution of plasma demonstrating macroscopic agglutination. The dilutions of the patient plasma or serum are performed in separate sample tubes rather than directly in the immunodiagnostic test device to prevent contamination of the sample with the reagent in the test device.

SUMMARY

Described herein are methods of determining a concentration of an analyte in a sample by in situ serial dilution. The methods include, but are not limited to, determining a titer of an antibody in a sample, determining antigen concentration, and generating a calibration curve. The disclosed methods find utility in immunodiagnostic testing. Methods have been discovered in which the sample is diluted in situ or directly in the test device (e.g., a gel test card) rather than in separate tubes. Surprisingly, the air gap between the incubation and reaction chambers was preserved while performing sample dilutions in the test device, and the sample did not become contaminated by reagent in the test device while being diluted in the test device.

In an embodiment, a method of determining the concentration of an analyte in a sample by in situ serial dilution is provided. In the method an immunodiagnostic test card comprising a substantially flat support that supports a plurality of vertically disposed microtubes is provided. Each microtube in the test card has an incubation chamber for receiving the sample and a reaction chamber comprising a separation matrix. Diluent is added to at least one of the incubation chambers. The sample is serially diluted directly into each of the incubation chambers having diluent therein. A reagent capable of complexing with the analyte to form a reagent-analyte complex is added to each of the incubation chambers having diluent and/or sample therein. The mixture of sample and reagent is exposed to sedimentation by gravitation and/or centrifugation. The concentration of the analyte is determined by determining a highest dilution of the sample at which a reagent-analyte complex is detected on or within the separation matrix.

In another embodiment, the method of determining the concentration of an analyte in a sample by in situ serial dilution comprises providing an immunodiagnostic test card comprising a substantially flat support that supports a plurality of vertically disposed microtubes. Each microtube has an incubation chamber for receiving the sample and a reaction chamber comprising a separation matrix and a reagent capable of complexing with the analyte to form a reagent-analyte complex. A diluent is added to at least one of the incubation chambers. The sample is serially diluted directly into each of the incubation chambers having diluent therein. The test card is exposed to sedimentation by gravitation and/or centrifugation. The concentration of the analyte is determined by determining a highest dilution of the sample at which a reagent-analyte complex is detected on or within the separation matrix.

BRIEF DESCRIPTION OF THE DRAWINGS

FIG. 2A is an image of test card results using a reference method. FIG. 2B is an image of test card results using a dilution in the test card method.

FIG. 3A is an image of test card results using the reference method. FIG. 3B is an image of test card results using the dilution in the test card method.

FIGS. 4A-4B are images of test card results using the reference method. FIGS. 4C-4D are images of test card results using the dilution in the test card method.

FIG. 5A is an image of test card results using the reference method. FIG. 5B is an image of test card results using the dilution in the test card method.

FIGS. 6A-6C are images of test card results using the reference method. FIGS. 6D-6F are images of test card results using the dilution in the test card method.

FIG. 7A is an image of test card results using the reference method. FIG. 7B is an image of test card results using the dilution in the test card method.

FIGS. 8A-8B are images of test card results using the reference method. FIG. 8C-8D are images of test card results using the dilution in the test card method.

FIG. 9A is an image of test card results using the reference method. FIG. 9B is an image of test card results using the reference method with contaminated wells (i.e., contaminated with gel and centrifuged prior to use). FIG. 9C is an image of test card results using the dilution in the test card method with contaminated wells.

FIGS. 10A-10B are images of test card results using the reference method. FIGS. 10C-10D are images of test card results using the reference method with contaminated wells. FIGS. 10E-10F are images of test card results using the dilution in the test card method with contaminated wells.

FIGS. 11A-11B are images of test card results using the reference method. FIGS. 11C-11D are images of test card results using the reference method with contaminated wells. FIGS. 11E-11F are images of test card results using the dilution in the test card method with contaminated wells.

FIGS. 12A-12B are images of test card results using the reference method. FIGS. 12C-12D are images of test card results using the reference method with contaminated wells. FIGS. 12E-12F are images of test card results using the dilution in the test card method with contaminated wells.

FIG. 13A is an image of test card results using the reference method. FIG. 13B is an image of test card results using the reference method with contaminated wells. FIG. 13C is an image of test card results using the dilution in the test card method with contaminated wells.

FIGS. 14A-14C are images of test card results using the reference method. FIGS. 14D-14F are images of test card results using the reference method with contaminated wells. FIGS. 14G-14I are images of test card results using the dilution in the test card method with contaminated wells.

FIG. 15A is an image of test card results using the reference method. FIG. 15B is an image of test card results using the reference method with contaminated wells. FIG. 15C is an image of test card results using the dilution in the test card method with contaminated wells.

FIGS. 16A-16B are images of test card results for the first plasma A sample. FIGS. 16C-16D are images of test card results for the second plasma A sample. FIGS. 16E-16F are images of test card results for the third plasma A sample.

FIGS. 17A-17D are images of test card results for the first plasma O sample. FIGS. 17E-17H are images of test card results for the second plasma O sample. FIGS. 17I-17J are images of test card results for the third plasma O sample.

FIG. 18A is an image of test card results using the reference method in which calibrated in serially diluted in tubes. FIG. 18B is an image of test card results using the dilution in the test card method.

FIG. 19A is an image of test card results using the reference method. FIG. 19B is an image of test card results using the dilution in the test card method.

DETAILED DESCRIPTION

Figure 1:
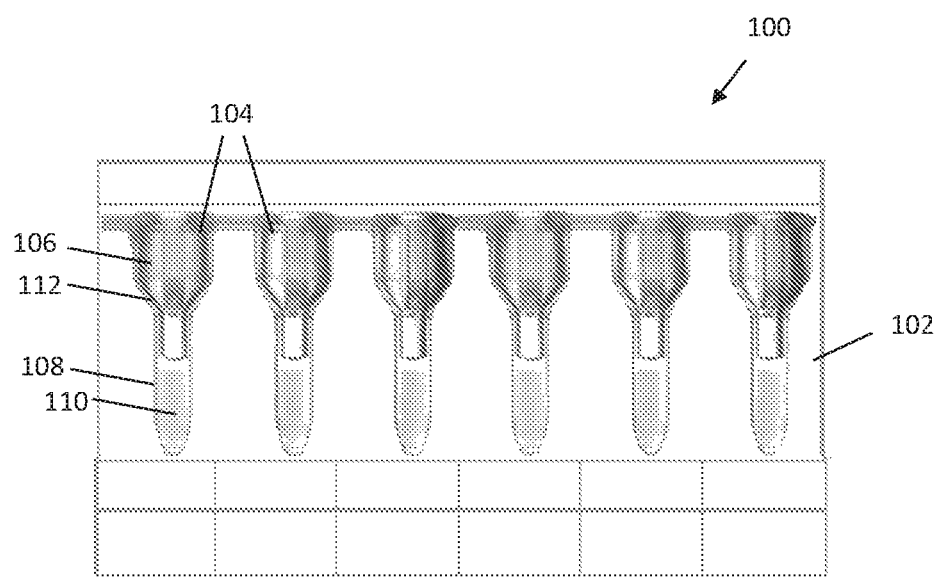
FIG. 1 is a front view of an immunodiagnostic test card that can be used in methods according to embodiments of the invention.
Figure 2A:
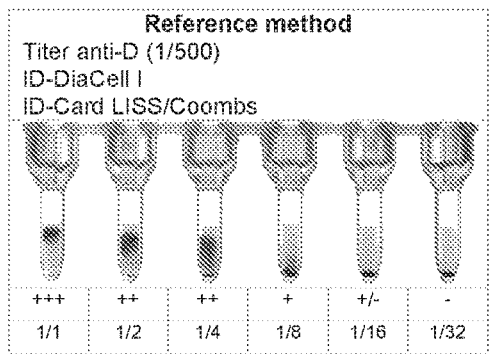
FIGS. 2A-2B show results from an anti-D titration experiment as described in Example 1 (anti-D plasma is prediluted 500×).
Figure 2B:
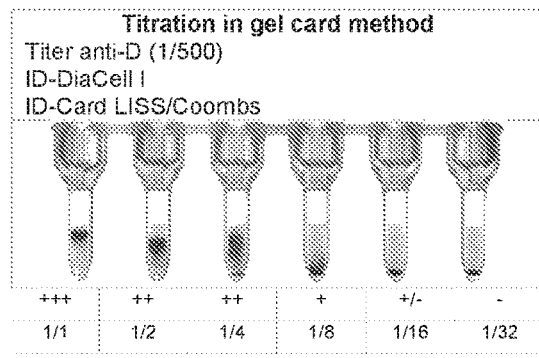
Figure 3A:
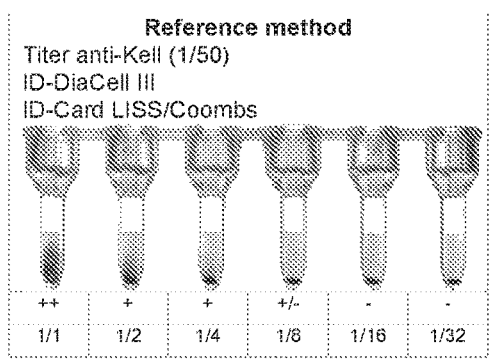
FIGS. 3A-3B show results from an anti-Kell titration experiment as described in Example 1 (anti-Kell is prediluted 50×).
Figure 3B:
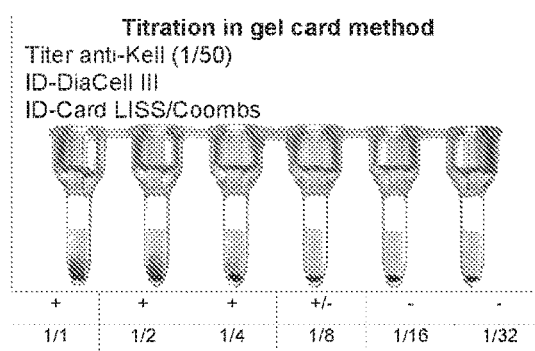
Figure 4A:
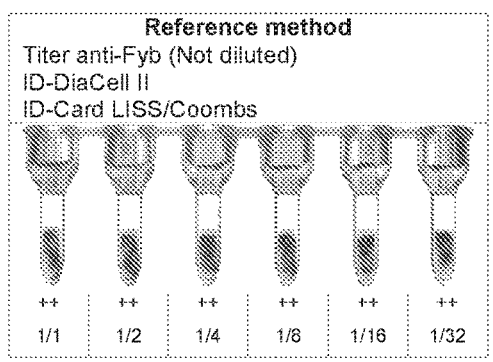
FIGS. 4A-4D show results from an anti-Fyb titration experiment as described in Example 1.
Figure 4B:
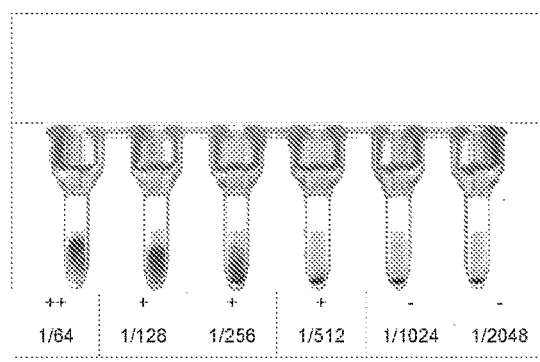
Figure 4C:
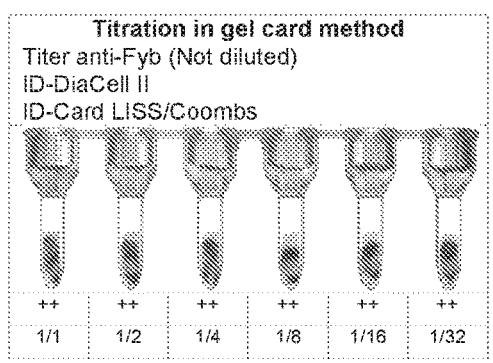
Figure 4D:
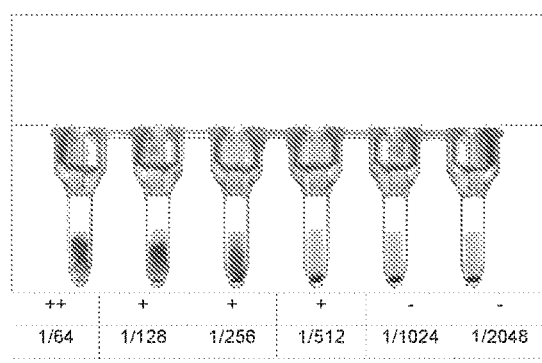
Figure 5A:
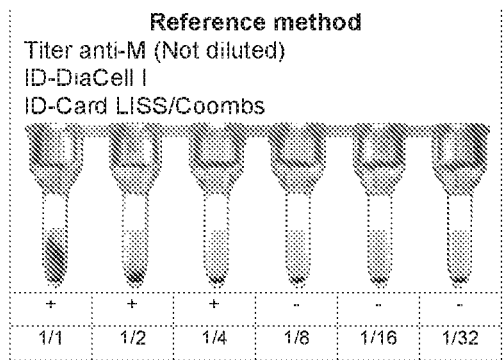
FIGS. 5A-5B show results from an anti-M titration experiment as described in Example 1.
Figure 5B:
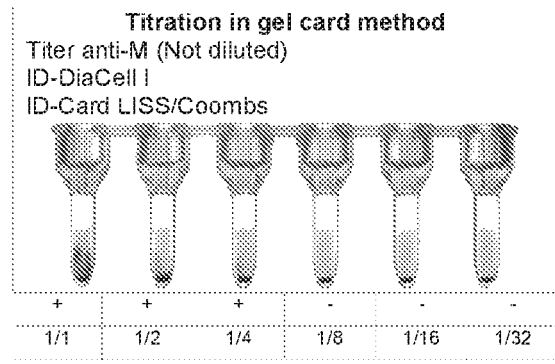
Figure 6A:
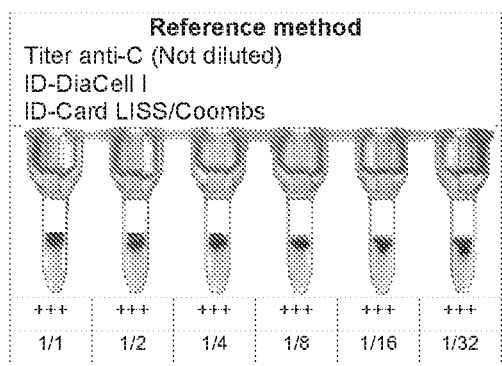
FIGS. 6A-6F show results from an anti-C titration experiment as described in Example 1.
Figure 6B:
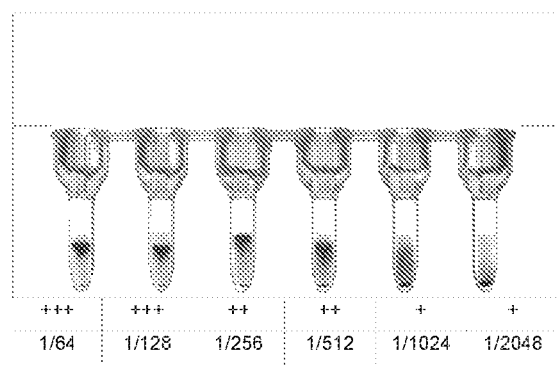
Figure 6C:
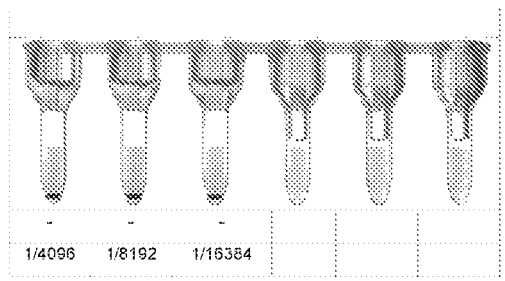
Figure 6D:
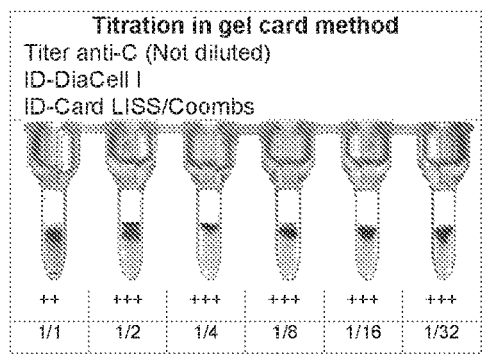
Figure 6E:
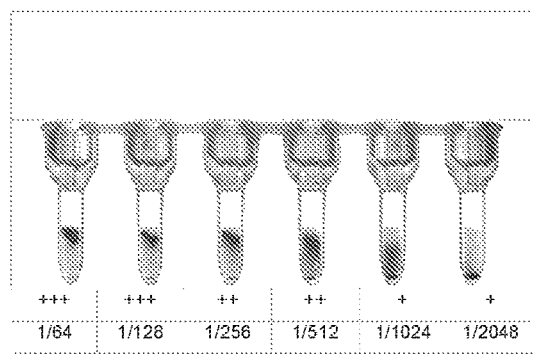
Figure 6F:
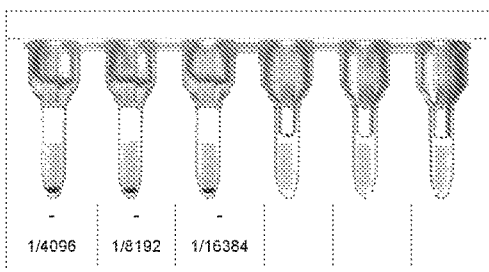
Figure 7A:
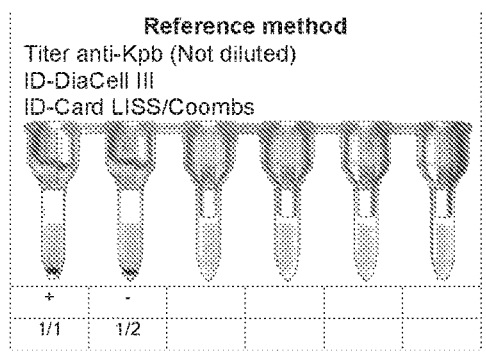
FIGS. 7A-7B show results from an anti-Kpb titration experiment as described in Example 1.
Figure 7B:
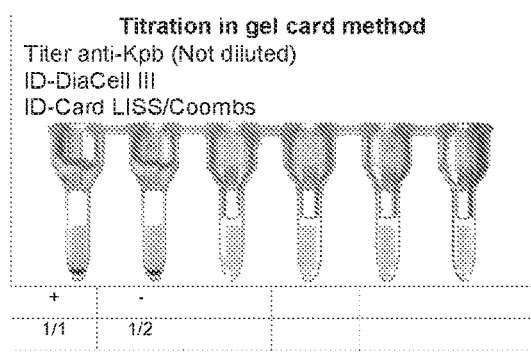
Figure 8A:
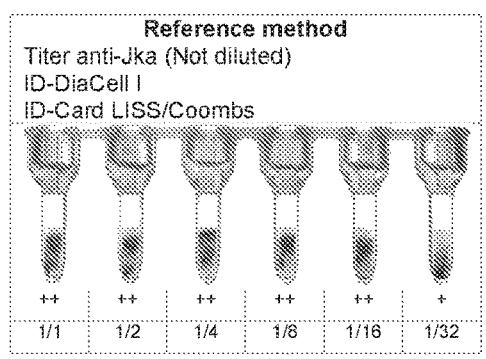
FIGS. 8A-8D show results from an anti-Jka titration experiment as described in Example 1.
Figure 8B:
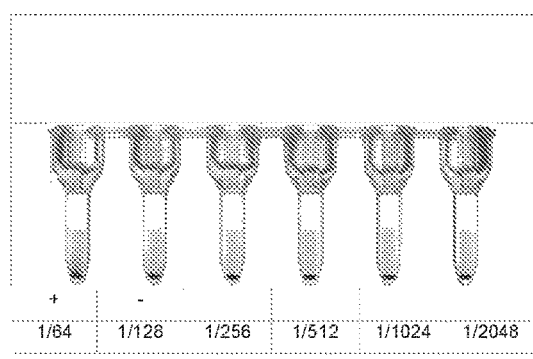
Figure 8C:
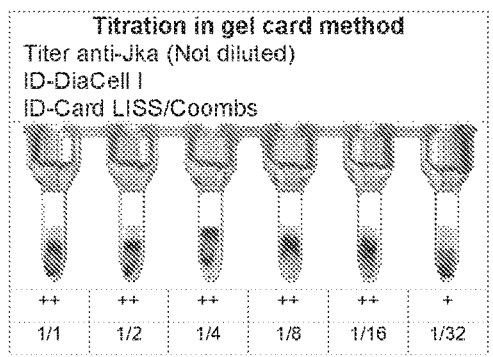
Figure 8D:
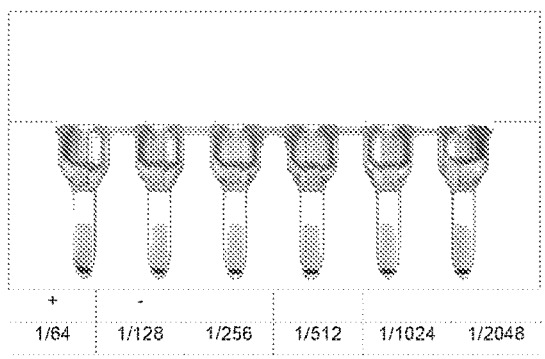
Figure 9A:
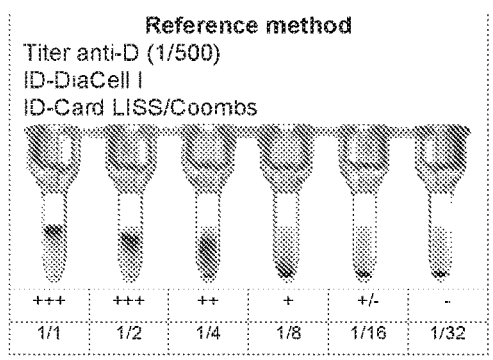
FIGS. 9A-9C show results from an anti-D incubation chamber AHG contamination experiment as described in Example 1.
Figure 9B:
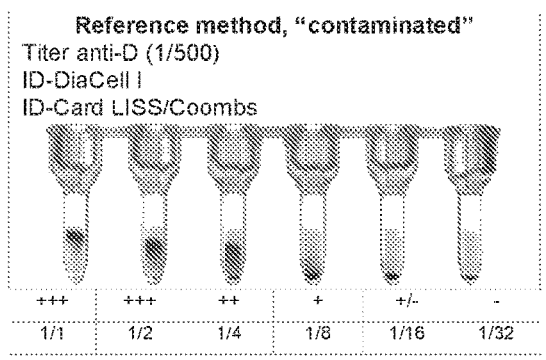
Figure 9C:
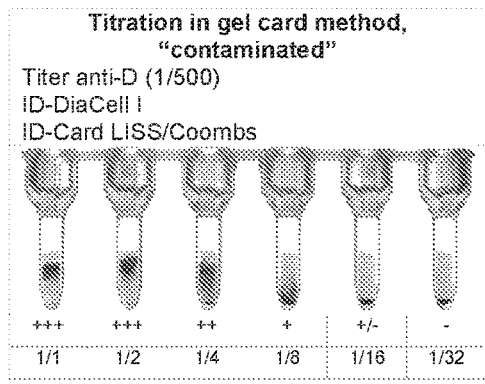
Figure 10A:
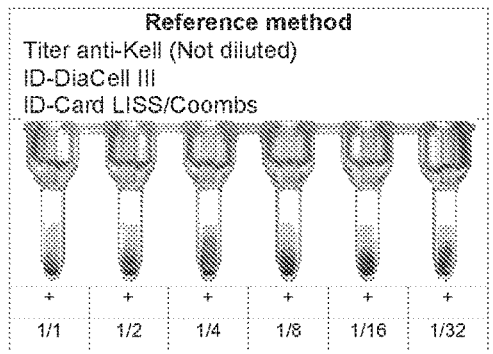
FIGS. 10A-10F show results from an anti-Kell incubation chamber AHG contamination experiment as described in Example 1.
Figure 10B:
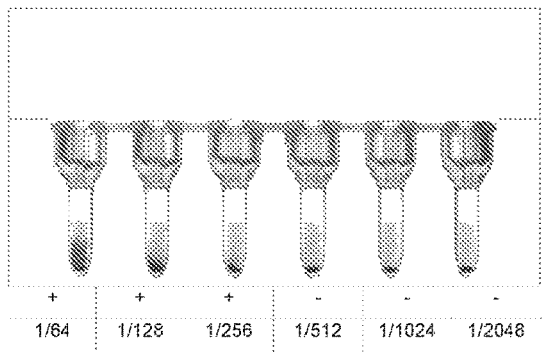
Figure 10C:
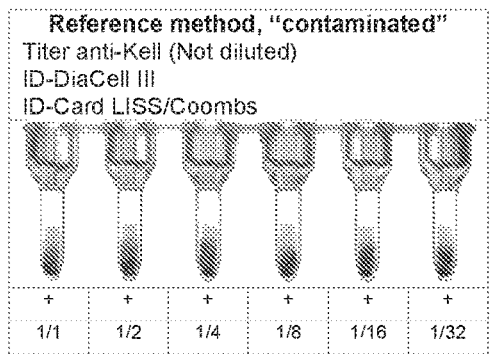
Figure 10D:
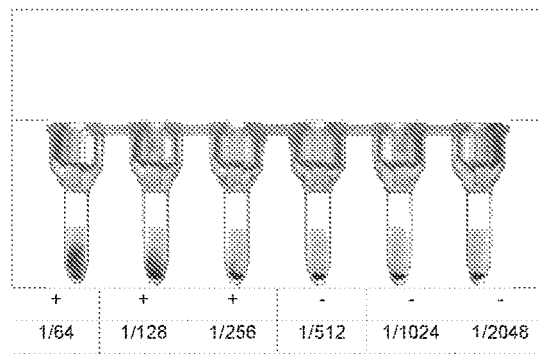
Figure 10E:
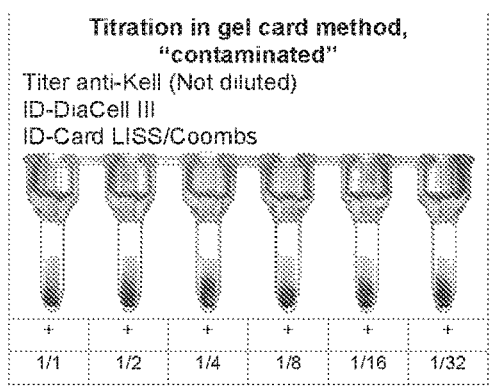
Figure 10F:
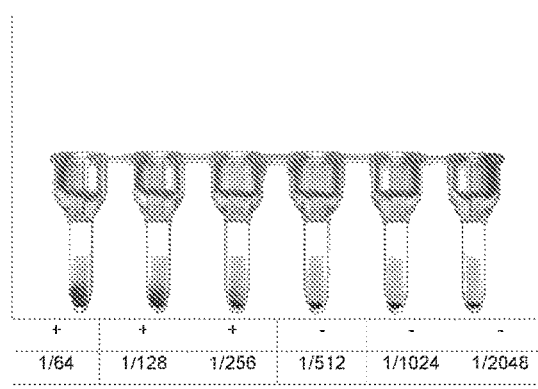
Figure 11A:
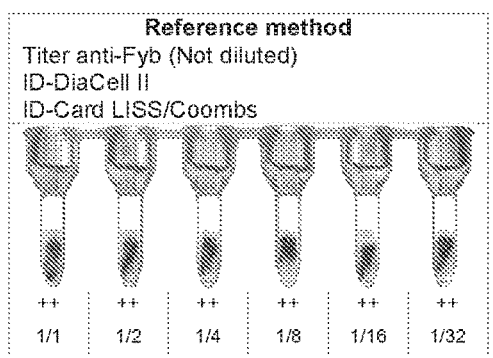
FIGS. 11A-11F show results from an anti-Fyb incubation chamber AHG contamination experiment as described in Example 1.
Figure 11B:
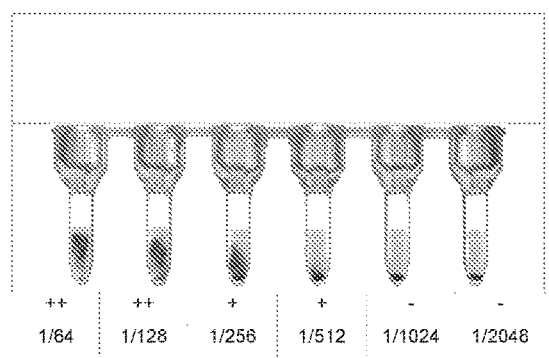
Figure 11C:
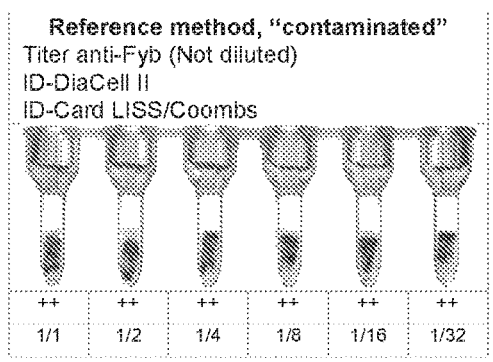
Figure 11D:
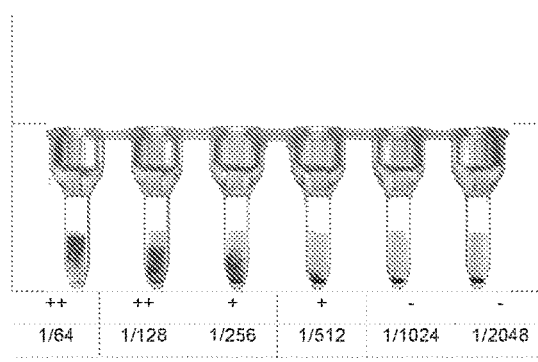
Figure 11E:
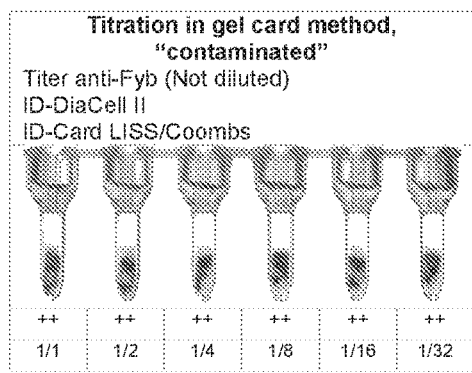
Figure 11F:
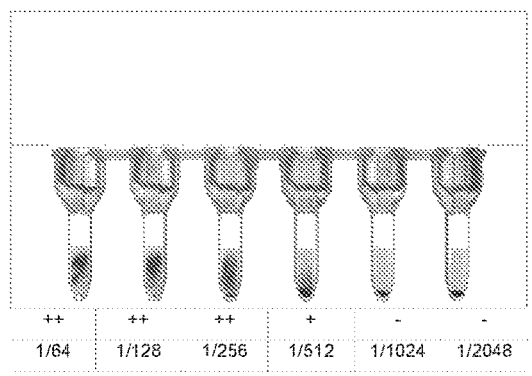
Figure 12A:
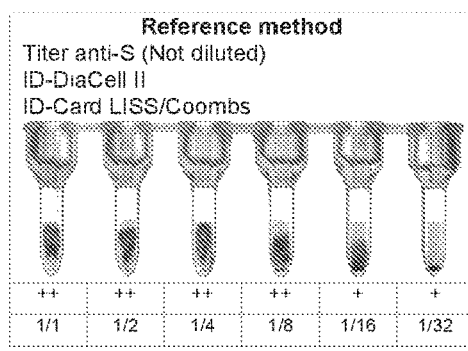
FIGS. 12A-12F show results from an anti-S incubation chamber AHG contamination experiment as described in Example 1.
Figure 12B:
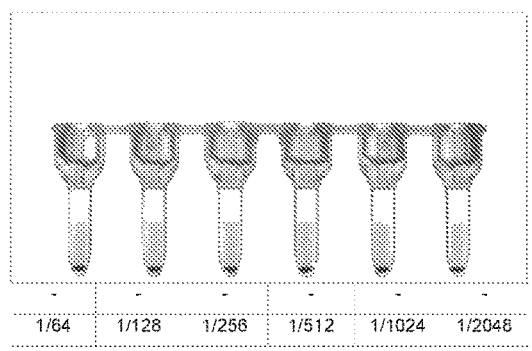
Figure 12C:
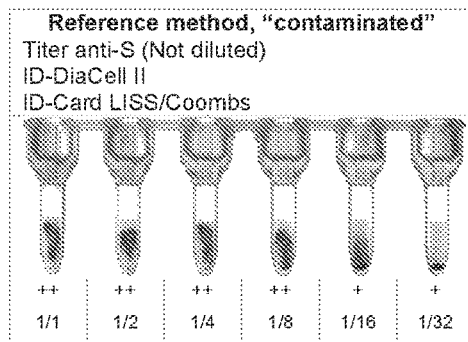
Figure 12D:
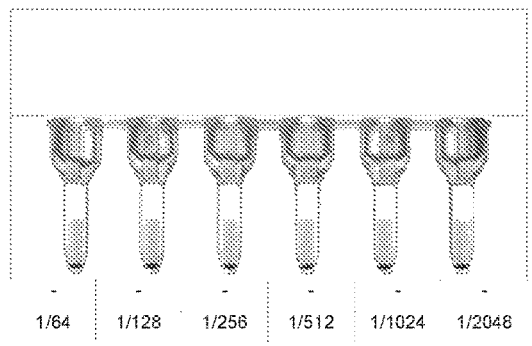
Figure 12E:
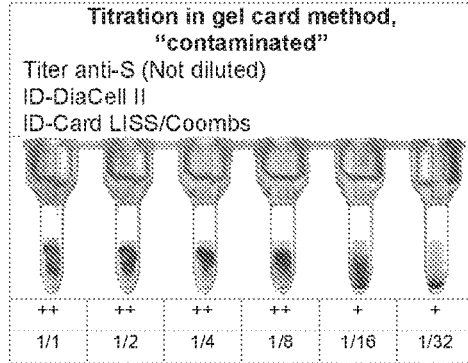
Figure 12F:
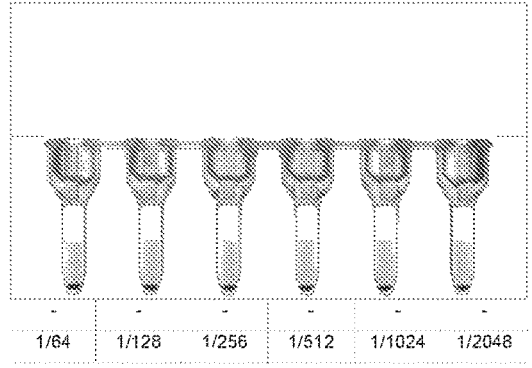
Figure 13A:
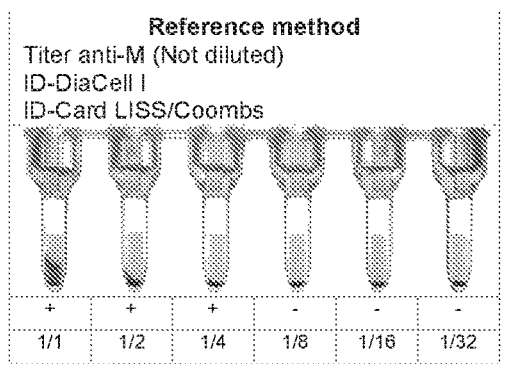
FIGS. 13A-13C show results from an anti-M incubation chamber AHG contamination experiment as described in Example 1.
Figure 13B:
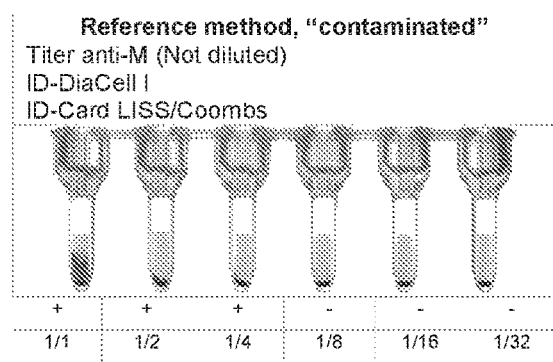
Figure 13C:
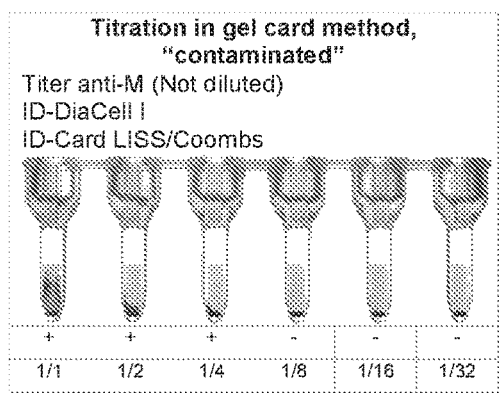
Figure 14A:
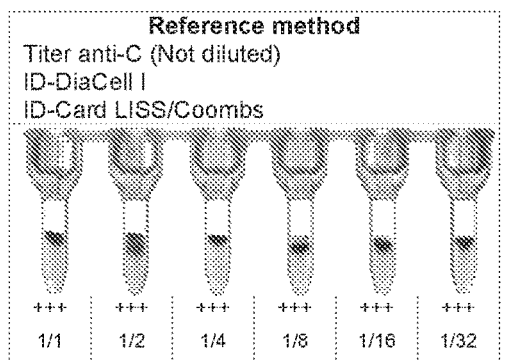
FIGS. 14A-14I show results from an anti-C incubation chamber AHG contamination experiment as described in Example 1.
Figure 14B:
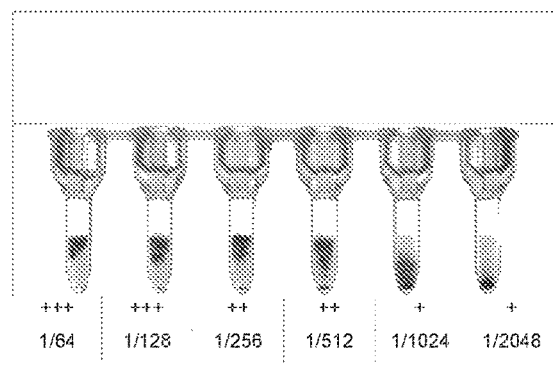
Figure 14C:
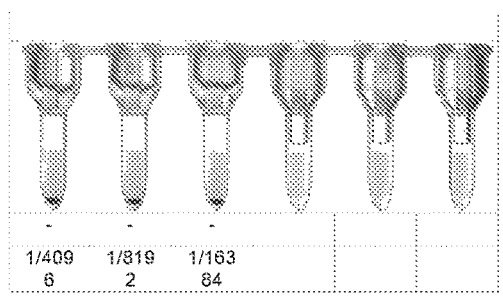
Figure 14D:
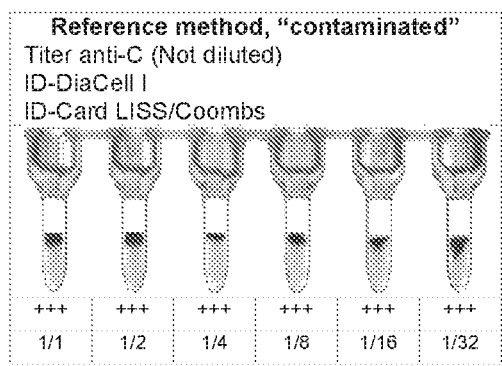
Figure 14E:
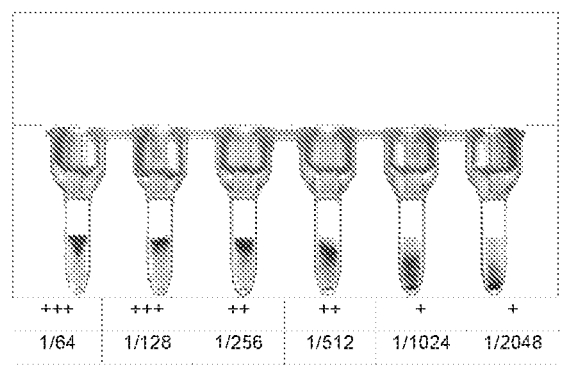
Figure 14F:
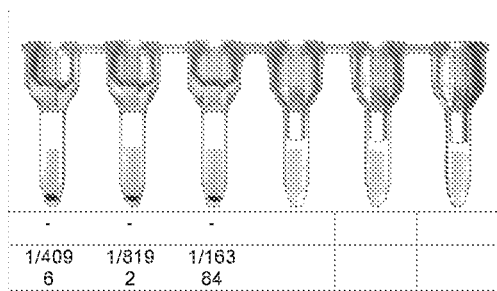
Figure 14G:
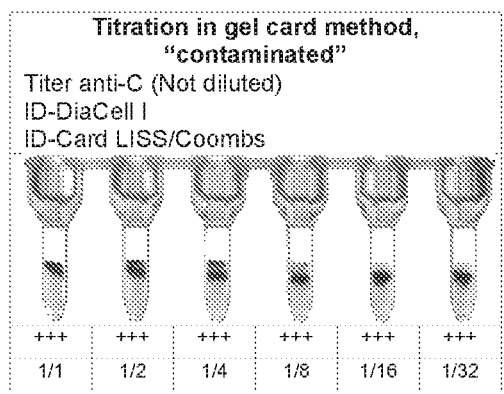
Figure 14H:
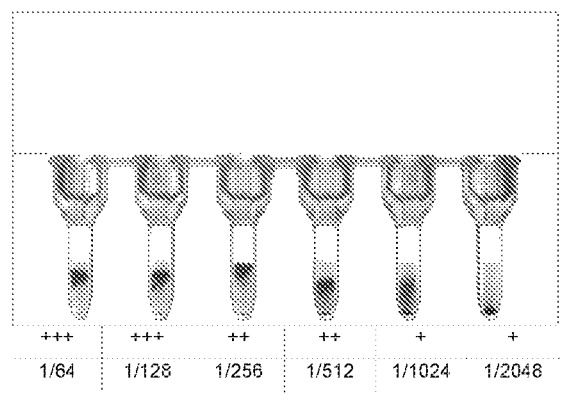
Figure 14I:
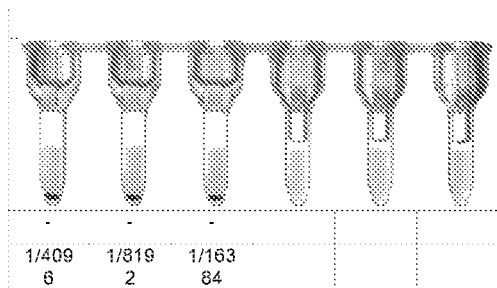
Figure 15A:
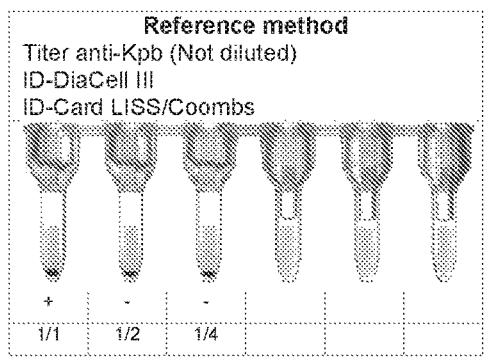
FIGS. 15A-15C show results from an anti-Kpb incubation chamber AHG contamination experiment as described in Example 1.
Figure 15B:
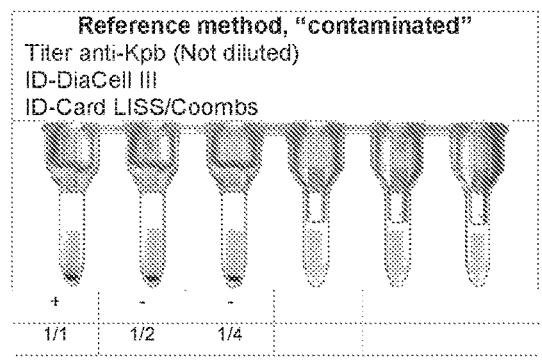
Figure 15C:
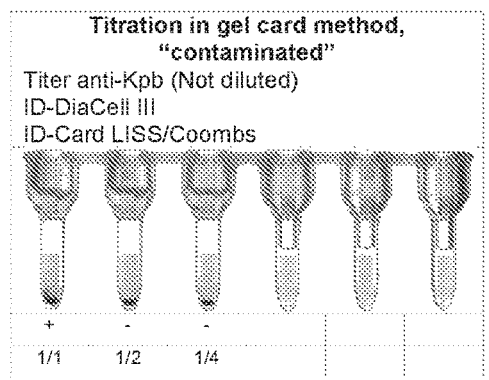
Figure 16A:
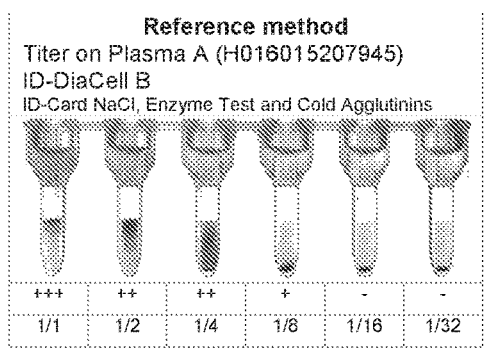
FIGS. 16A-16F show results from a reverse typing titration experiment with three plasma A samples as described in Example 1. Each sample was tested with the reference method and with the dilution in the test card method.
Figure 16B:
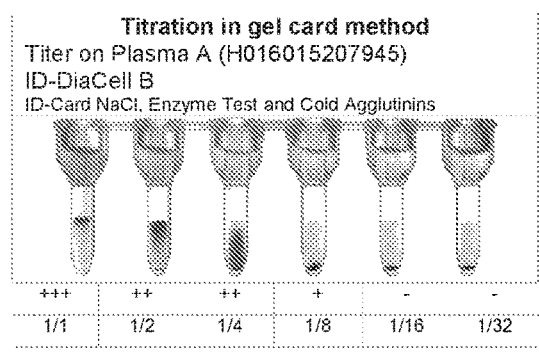
Figure 16C:
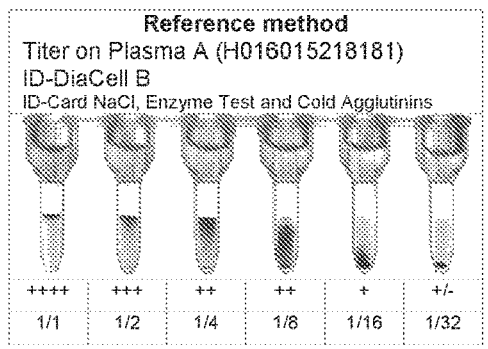
Figure 16D:
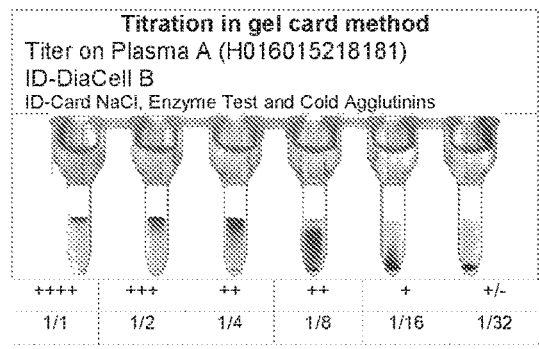
Figure 16E:
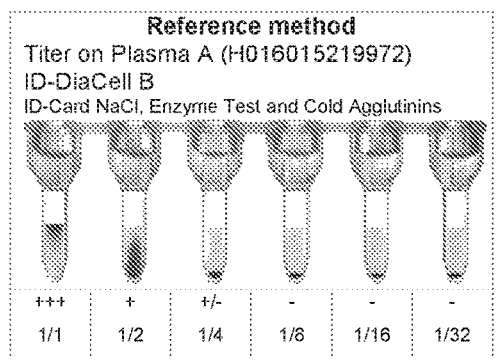
Figure 16F:
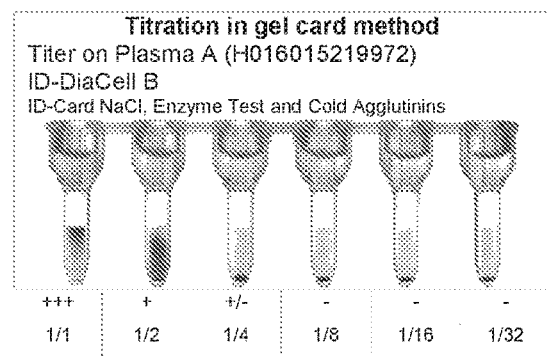
Figure 17A:
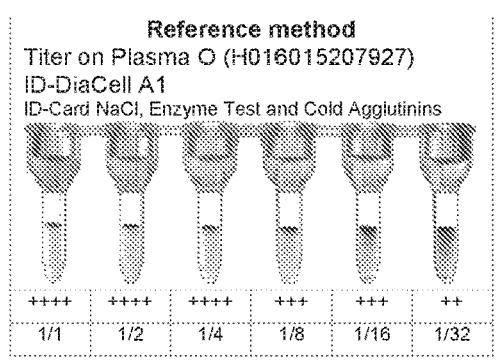
FIGS. 17A-17J show results from a reverse typing titration experiment with three plasma O samples as described in Example 1. Each sample was tested with the reference method and with the dilution in the test card method.
Figure 17B:
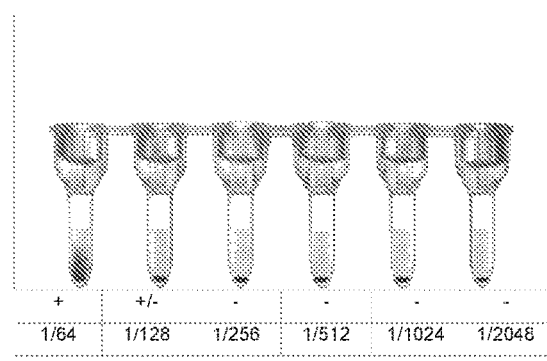
Figure 17C:
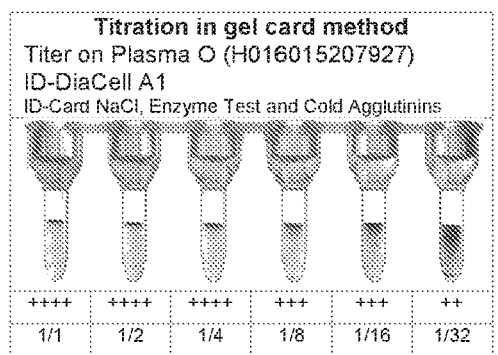
Figure 17D:
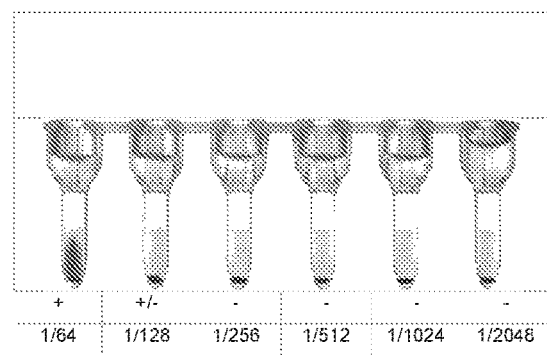
Figure 17E:
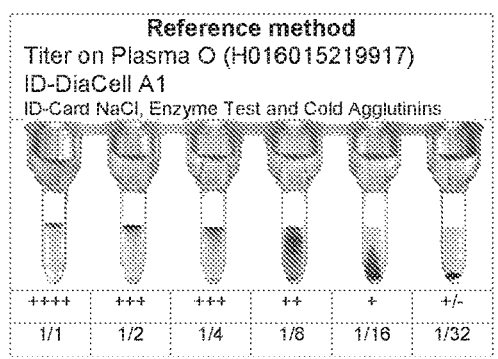
Figure 17F:
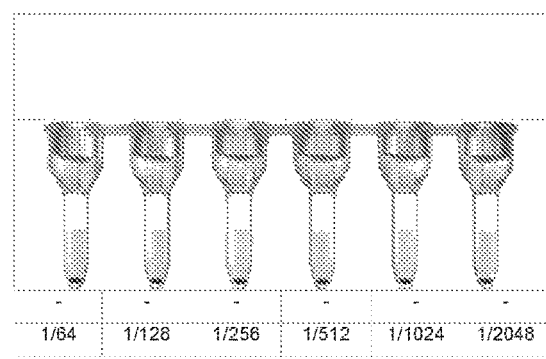
Figure 17G:
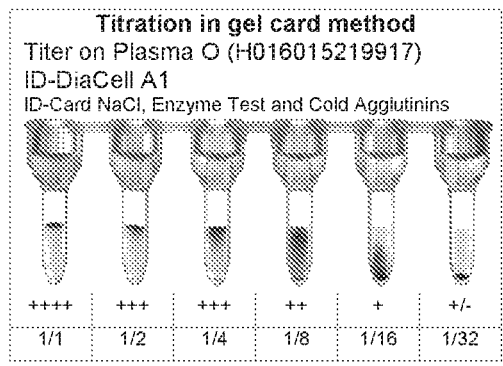
Figure 17H:
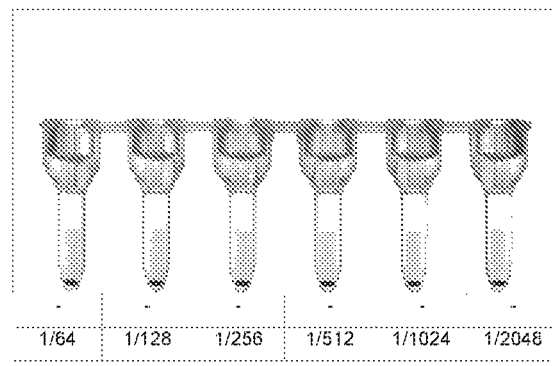
Figure 17I:
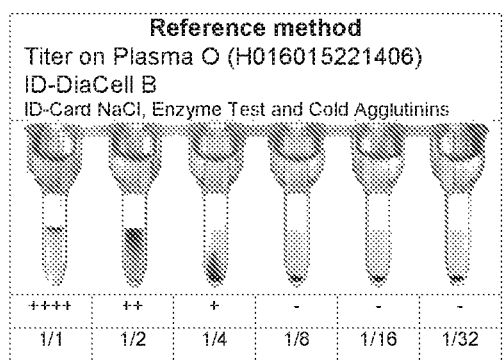
Figure 17J:
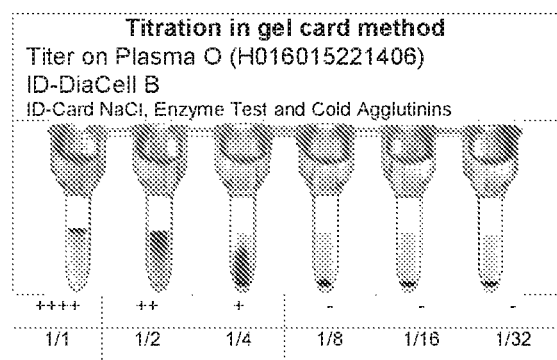

Provided herein are methods of determining an analyte concentration in a sample by serial dilution.

I. DEFINITIONS

The term "a" or "an" is intended to mean "one or more." The term "comprise" and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

The term "antibody" refers to a polypeptide of the immunoglobulin family or a polypeptide comprising fragments of an immunoglobulin that is capable of noncovalently, reversibly, and in a specific manner binding to a corresponding antigen. The term includes, but is not limited to, polyclonal or monoclonal antibodies of the isotype classes IgA, IgD, IgE, IgG, and IgM.

The term "antigen" refers to a molecule, compound, or complex that is recognized by an antibody, i.e., can be specifically bound by the antibody. The term can refer to any molecule that can be specifically recognized by an antibody, including but not limited to, a protein (e.g., a blood group protein, a native protein, a fragment of a native protein, or a recombinant protein), a polypeptide, a polysaccharide, a lipid, a lipid complexed with a protein or a polysaccharide, a carbohydrate, chemical moiety, or combinations thereof.

The term "protein" refers to an amino acid polymer or a set of two or more interacting or bound amino acid polymers.

The term "serial dilution" refers to a stepwise dilution of a substance in solution. Each steps do not necessarily have identical dilution factors.

The wording "providing an immunodiagnostic test card" refers to the fact that the method is performed using said immunodiagnostic test card.

II. METHODS

A method of determining a concentration of an analyte in a sample by in situ serial dilutions of the sample (e.g., plasma, serum, calibrator/standard) will now be described. In some embodiments, the analyte is an antibody directed against a red blood cell antigen and the antibody includes, but is not limited to, anti-A antibody, anti-B antibody (or anti-ABO antibody), anti-C antibody, anti-c antibody, anti-D antibody, anti-E antibody, anti-e antibody, anti-Fya antibody, anti-Fyb antibody, anti-Jka antibody, anti-Kell antibody, anti-k antibody, anti-Kpa antibody, anti-Kpb antibody, anti-M antibody, anti-N antibody, anti-S antibody, and anti-s antibody. In certain embodiments, the analyte is an antigen. In some embodiments, the analyte is an antibody directed against antigen coated microspheres. In certain embodiment, the analyte is an antigen captured by antibody coated microspheres. In some embodiments, the analyte is any other ligand, e.g., biotin or streptavidin. As used herein, a "ligand" is a substance that forms a complex with a biomolecule to serve a biological purpose.

In an embodiment, the method comprises providing an immunodiagnostic test card 100 (FIG. 1). The test card 100 comprises a substantially flat support 102 that supports a plurality of vertically disposed microtubes (or test units) 104 (e.g., at least one, two, three, four, five, six, seven or eight), each microtube having an incubation chamber 106 for receiving the sample and a reaction chamber 108 comprising a separation matrix 110. The test card 100 and microtubes 104 can be formed of materials including, but not limited to, polyethylene, polyvinyl chloride, or polystyrene. The microtubes 104 can be glued or welded to an upper portion of the test card 100 or can be manufactured integrally with the test card by, for example, blister packaging. The microtubes 104 are generally cylindrical in shape with the incubation chamber 106 having a larger diameter than the reaction chamber 108. In some embodiments, a portion of the microtube 104 between the incubation chamber 106 and the reaction chamber 108 has a tapering diameter 112.

In some embodiments, the reaction chamber 108 comprises at least a separation matrix (for example a gel) and a supernatant (e.g., a liquid supernatant). In some embodiments, the reaction chamber 108 further comprises a reagent. In some embodiments, the reagent (or at least one of the reagents) is present in the supernatant. The reagent(s) is(are) capable of complexing (e.g., binding) with the analyte (or with one of the analytes) to form a reagent-analyte complex. In some embodiments, the reagent comprises a coated particle (e.g., a latex particle, microsphere or microparticle) or a red blood cell (RBC) having an antigen, antibody or any other analyte ligand (e.g., streptavidin) thereon. The antigen on the RBC will depend on the antibody to be titrated. For example, in an embodiment in which the antibody is an anti-D antibody, the antigen on the RBCs will be D antigen. In some embodiments, the reaction chamber 108 further comprises a reticulation agent, which can be present, for example, in the supernatant and/or in the separation matrix 110. As used herein, a reticulation agent is a biomolecule that cross links sensitized red blood cell or sensitized latex particles. Exemplary reticulation agents include, but are not limited to, a secondary antibody, (e.g., antihuman globulin or anti-human IgA antibody), Protein A, and a ligand (e.g., streptavidin).

In some embodiments, the separation matrix 110 is a gel, e.g., a polyelectrolyte gel comprising dextran acrylamide. In some embodiments, the separation matrix 110 is an inert material including, but not limited to, agarose, polyacrylamide, polydextran, styrene-divinylbenzene polymers, or glass beads.

In certain embodiments, the microtube 104 further comprises an air gap above the separation matrix 110 (e.g., between the incubation chamber 106 and the reaction chamber 108). In some embodiments, the microtube 104 comprises an oil layer (or any low density immiscible compound, e.g., a low density immiscible compound as disclosed in patent application WO2016/184924) above the separation matrix 110. Exemplary oils in the oil layer can include, but are not limited to, synthetic oil, organic oil, mineral oil, or paraffinic oil. In some embodiments, the microtube 104 comprises an air gap and an oil layer between the incubation chamber 106 and the reaction chamber 108.

The next step of the method comprises adding diluent (e.g., buffer, AB plasma, AB serum, or a solution having 0.9% sodium chloride and 6% bovine serum albumin) to at least one of the incubation chambers 106 in the test card 100. In some embodiments, diluent is added to the incubation chambers 106 starting with the second incubation chamber. In some embodiments, 5-200 microliters of diluent is added to at least one of the incubation chambers 106. The maximum volume of diluent added to the incubation chamber will depend on the capacity of the incubation chamber and the dilution factor.

In the next step of the method, the sample is serially diluted directly into each of the incubation chambers 106 having diluent therein. In some embodiments, the sample is diluted into incubation chambers across multiple test cards. In certain embodiments, the serial dilution is a two-fold or less dilution (e.g., 1:0.1, 1:0.5, 1:0.75, etc.). In some embodiments, the serial dilution is a two-fold or more serial dilution (e.g., at least 1:1, 1:2, 1:3, or more dilution). In an exemplary two-fold serial dilution embodiment, 5-200 microliters (or a volume equal to the amount of diluent) of the sample is added to the first two incubation chambers. In the second incubation chamber, the sample is mixed with diluent by, for example, pipetting up and down (manually or automatically) two to five or more times. In embodiments having an air gap or an oil layer between the incubation and reaction chambers, the sample is mixed with the diluent without disturbing the air gap or oil layer. Using a clean pipette tip to prevent carry over, a volume (e.g., 5-200 microliters) of the mix from the second incubation chamber is then added to the next incubation chamber, mixed, and so on until the last incubation chamber from which 5-200 microliters is removed and discarded. For example, in an embodiment, 10 microliters of the mix is removed from the second incubation chamber, is added to the next incubation chamber and is mixed. 10 microliters of the mix in the third incubation chamber is then transferred to the next incubation chamber, and so on until the last incubation chamber from which 10 microliters is removed and discarded. An exemplary resulting dilution factor in the incubation chambers is 1×, 2×, 4×, 8×, 16× and 32×.

In some embodiments including embodiments in which the reaction chamber 108 does not comprise a reagent, the next step of the method comprises adding a reagent to each of the incubation chambers 106. In some embodiments, the reagent is mixed with the diluted sample after being added to the incubation chamber 106. In some embodiment, coated microspheres or microparticles are used to capture corresponding antibodies or antigens.

In the next step of the method, the test card 100 is optionally incubated at 37° C., room temperature, or 4° C. for an appropriate amount of time (e.g., 5-15 minutes) to allow the reagent to interact with the diluted sample. The test card 100 is then exposed to sedimentation (e.g., by centrifugation or gravitation) to separate agglutinated RBCs from non-agglutinated RBCs based on size. In an embodiment, the test card 100 is centrifuged for an appropriate amount of time and at a sufficient speed (e.g., 5-10 minutes at 85×g) to separate agglutinated RBCs from non-agglutinated RBCs. Agglutinated RBCs are captured at the top of or within the separation matrix 110, and non-agglutinated RBCs form a pellet at the bottom of the microtube 104.

In embodiments in which the titer of an antibody is being determined, the last step of the method comprises determining the highest dilution of the sample at which a reagent-antibody complex (e.g., an agglutinate) is detected on or within the separation matrix 110 (e.g., visual detection of the reagent-antibody complex is based on the instructions for use of the corresponding test card). In some embodiments, the antibody titer is the highest dilution of the sample for which a reagent-antibody complex is observed corresponding to a reaction strength of "+". In some embodiments, the reagent-antibody complex is detected visually or optically. In certain embodiments, the method further comprises determining the reaction grade for each dilution. In some embodiments, the method further comprises determining an antibody titer score and the antibody titer score is the sum of the score values assigned to each reaction.

In embodiments in which the concentration of an antigen is being determined, the last step of the method comprises determining the highest dilution of the sample at which an antihuman globulin-antigen complex is detected on or within the separation matrix 110. In certain embodiments, the antihuman globulin-antigen complex is detected visually or optically.

Additional Disclosure and Claimable Subject Matter

Item 1. A method of determining a concentration of an analyte in a sample by in situ serial dilution, the method comprising:
providing an immunodiagnostic test card, the test card comprising a substantially flat support that supports a plurality of vertically disposed microtubes, each microtube having an incubation chamber for receiving the sample and a reaction chamber comprising a separation matrix, wherein the reaction chamber comprises a reagent capable of complexing with the analyte to form a reagent-analyte complex;
adding a diluent to at least one of the incubation chambers;
serially diluting the sample directly into each of the incubation chambers having diluent therein;
exposing the test card to sedimentation by gravitation and/or centrifugation; and
determining the concentration of the analyte by determining a highest dilution of the sample at which a reagent-analyte complex is detected on or within the separation matrix.

Item 2. The method of Item 1, wherein the determining the concentration of the analyte step comprises determining a titer of an antibody and the titer is the highest dilution of the sample for which a reagent-antibody complex is observed corresponding to a reaction strength of "+".

Item 3. The method of Item 2, further comprising determining an antibody endpoint and the antibody endpoint is the highest dilution of the sample having visible reagent-antibody complexes.

Item 4. The method of Item 2 or 3, further comprises determining an antibody titer score and the antibody titer score is the sum of the score values assigned to each reaction.

Item 5. The method of Item 2, wherein the determining the concentration of the analyte step comprises determining the concentration of an antigen.

Item 6. The method of any one of Items 1-5, wherein the separation matrix is a gel comprising dextran acrylamide.

Item 7. The method of any one of Items 1-6, wherein reaction chamber comprises a reticulation agent.

Item 8. The method of Item 7, wherein the reticulation agent is a secondary antibody.

Item 9. The method of Item 8, wherein the secondary antibody is antihuman globulin or anti-human IgA antibody.

Item 10. The method of Item 1, wherein the serially diluting the sample step comprises serially diluting the sample directly into each of the incubation chambers in the same test card or between test cards.

Item 11. The method of any one of Items 1-10, wherein the reagent comprises a red blood cell or a coated particle having an antigen or antibody thereon.

Item 12. The method of any one of Items 2-4, wherein the antibody is directed against a red blood cell antigen.

Item 13. The method of Item 12, wherein the antibody is selected from the group consisting of anti-A antibody, anti-B antibody, anti-D antibody, anti-C antibody, anti-c antibody, anti-E antibody, anti-e antibody, antidy-Fya antibody, anti-Fyb antibody, anti-Kell antibody, anti-k antibody, anti-Kpa antibody, anti-Kpb antibody, anti-M antibody, anti-N antibody, anti-S antibody, and anti-s antibody.

Item 14. The method of any one of Items 1-13, wherein each microtube further comprises an air gap between the incubation chamber and the reaction chamber.

Item 15. The method of any one of Items 1-14, wherein each microtube further comprises a low density immiscible compound between the incubation chamber and the reaction chamber.

Item 16. The method of Item 15, wherein the low density immiscible compound comprises an oil selected from the group consisting of synthetic oil, organic oil, mineral oil, and paraffinic oil.

Item 17. The method of any one of Items 1-16, further comprising, after the step of serially diluting the sample directly into each of the incubation chambers having diluent therein, adding an additional reagent to each of the incubation chambers having diluent and/or sample therein, wherein the reagent is capable of complexing with an analyte to form a reagent-analyte complex.

Item 18. The method of Item 17, further comprising incubating the test card after the step of adding the additional reagent to each of the incubation chambers having diluent and/or sample therein.

Item 19. The method of any one of Items 1-18, wherein the serially diluting the sample step comprises at least a two-fold serial dilution of the sample into each of the incubation chambers having diluent therein.

Item 20. The method of any one of Items 1-19, wherein the serially diluting the sample step comprises less than a two-fold serial dilution of the sample into each of the incubation chambers having diluent therein.

Item 21. The method of any one of Items 1-20, wherein the serially diluting the sample step comprises a two-fold serial dilution of the sample into each of the incubation chambers having diluent therein.

Item 22. The method of any one of Items 1-21, wherein the sample is selected from the group consisting of serum, plasma, and a calibrator.

Item 23. The method of any one of Items 1-22, wherein the analyte is an antibody or an antigen.

III. EXAMPLES

Example 1—Comparison of Dilution of Sample Directly in a Microtube to Reference Dilution Method In this example, dilution of the sample directly in a microtube was compared to dilution of the sample in separate tubes.

Materials
1. ID-Cards
   ID-Card LISS/Coombs (DiaMed GmbH, Bio-Rad)
   ID-Card NaCl, Enzyme Test and Cold Agglutinins (DiaMed GmbH, Bio-Rad)
2. Reagent red blood cells
   ID-DiaCell I, II, III (DiaMed GmbH, Bio-Rad)
   ID-DiaCell ABO (DiaMed GmbH, Bio-Rad)
3. Dilution Medium—ID-Titration Solution, (DiaMed GmbH, Bio-Rad)
4. Samples
   Anti-D, from human patients, diluted 1:500 in 0.9% NaCl/6% BSA
   Anti-Kell, diluted 1:50 in ID-Titration Solution
   Anti-Fyb, anti-S, anti-M, anti-C, anti-Kpb, anti-Jka from human patients
   Fresh plasma from donors: 3 plasma A and 3 plasma O
5. Dilution tubes—Hemolysis glass tubes, Ratiolab (Ref. 2600131)

Method
1. Reference Method for Dilution
   a. Identified the suspension tubes according to the number of dilution steps to be performed, e.g. tube 1 (undiluted sample, 1/1), tube 2 (dilution 1/2), tube 3 (dilution 1/4), etc.
   b. Dispensed 500 µl of ID-Titration Solution in each suspension tube except in tube 1 (undiluted).
   c. Dispensed 500 µl of sample in tube 1 and tube 2. Change tips and mixed the content of tube 2 by pipetting up and down 4-5 times.
   d. From this mix, removed 500 µl and dispensed it to tube 3. Changed tips and mixed the content of tube 3 by pipetting up and down 4-5 times.
   e. Continued the same process for all dilutions using clean tips to mix and transfer to each dilution. From the final tube, removed 500 µl of diluted sample and saved it for use if further dilutions were required.
   Note that the volume used to perform the serial twofold dilution (here 500 µl) must be adapted to the sample volume availability as well as to the suspension tubes used.
   f. Proceeded immediately to testing in ID-Card LISS/Coombs or ID-Card NaCl, Enzyme Test and Cold Agglutinins, as follows:
      Identified ID-Card microtubes for the appropriate dilutions.
      Transferred 50 µl of reagent red blood cells in each microtube, followed by 25 µl (for ID-Card LISS/Coombs) or 50 µl (for ID-Card NaCl, Enzyme Test and Cold Agglutinins) of each diluted sample, from the highest to the lowest dilution.
      Incubated 15 min at 37° C. in ID-Incubator for ID-Card LISS/Coombs or 10 min at RT for ID-Card NaCl, Enzyme Test and Cold Agglutinins.
      Centrifuged 10 min the ID-Cards in the ID-Centrifuge.
      Read and recorded the reaction results.
2. Dilution in the Test Card Method
   a. Identified ID-Card microtubes for the appropriate dilutions.
   b. Dispensed 25 µl (for ID-Card LISS/Coombs) or 50 µl (for ID-Card NaCl, Enzyme Test and Cold Agglutinins) of ID-Titration Solution in each ID-Card microtubes with the exception of the first microtube (undiluted sample).
   c. Dispensed 25 µl (for ID-Card LISS/Coombs) or 50 µl (for ID-Card NaCl, Enzyme Test and Cold Agglutinins) of sample in ID-Card microtube 1 and 2. Changed tips and mixed the content of microtube 2 by pipetting up and down 4-5 times.
   d. From this mix, removed 25 µl (for ID-Card LISS/Coombs) or 50 µl (for ID-Card NaCl, Enzyme Test and Cold Agglutinins) and dispensed in microtube 3. Changed tips and mixed the content of microtube 3 by pipetting up and down 4-5 times.
   e. Continued the same process for all dilutions using clean tips to mix and transfer to each dilution. From the final microtube, removed 25 µl (for ID-Card LISS/Coombs) or 50 µl (for ID-Card NaCl, Enzyme Test and Cold Agglutinins) of diluted sample.
   f. Immediately after dilution, added 50 µl of reagent red blood cells into each microtube.
   g. Incubated 15 min at 37° C. in ID-Incubator for ID-Card LISS/Coombs or 10 min at room temperature for ID-Card NaCl, Enzyme Test and Cold Agglutinins.
   h. Centrifuged 10 min the ID-Cards in the ID-Centrifuge.
   i. Read and recorded the reaction results.
3. AHG Contamination of the Incubation Chamber
   Incubation chambers were artificially contaminated with the AHG of the LISS/Coombs by shaking the test card until gel and supernatant were visually observed in the incubation chambers. Then ID-Cards were recovered by centrifugation, 10 min at 85×g before use as recommended by the supplier.

Results

Reaction grade and sample dilution are reported in FIGS. 2A-17J. All tests were performed simultaneous with the reference method. Images of indirect antiglobulin (antibody screening) titration test cards are shown in FIGS. 2A-8D. Images of tests card in which the wells were contaminated with AHG and then centrifuged prior to use in an indirect antiglobulin titration test card are shown in FIGS. 9A-15C. Images of reverse typing test cards are shown in FIGS. 16A-17J. The inventor observed that the air gap between the incubation chamber and reaction chamber was easily preserved while performing serial dilutions in the incubation chambers.

The titer and agglutination score results for each titration are shown in Table 1. The titer is the reciprocal the highest dilution producing a "+" reaction, and the strength of reactions were scored as described in the AABB Technical Manual (for each dilution, a score value is reported based on the reaction grade and summed over all dilutions). The endpoint is the reciprocal of the highest dilution with visible aggregates.

TABLE 1

Titers, Scores and Endpoints

| Test | Antibody | Method | Titer | Score | Endpoint |
|------|----------|--------|-------|-------|----------|
| IAT | Anti-D | Reference method | 8 | 33 | 16 |
| | | Dilution in the test card method | 8 | 33 | 16 |
| | Anti-Kell | Reference method | 4 | 20 | 8 |
| | | Dilution in the test card method | 4 | 17 | 8 |
| | Anti-Fyb | Reference method | 512 | 71 | 512 |
| | | Dilution in the test card method | 512 | 71 | 512 |
| | Anti-M | Reference method | 4 | 12 | 4 |
| | | Method 3 | 4 | 15 | 4 |
| | Anti-C | Reference method | 2048 | 106 | 2048 |
| | | Dilution in the test card method | 2048 | 104 | 2048 |
| | Anti-Kpb | Reference method | 1 | 5 | 1 |
| | | Dilution in the test card method | 1 | 5 | 1 |
| | Anti-Jka | Reference method | 64 | 50 | 64 |
| | | Dilution in the test card method | 64 | 50 | 64 |
| | Anti-D | Reference method | 8 | 35 | 16 |
| | | Reference method contaminated | 8 | 35 | 16 |
| | | Dilution in the test card method contaminated | 8 | 35 | 16 |
| | Anti-Kell | Reference method | 256 | 45 | 256 |
| | | Reference method contaminated | 256 | 45 | 256 |
| | | Dilution in the test card method contaminated | 256 | 45 | 256 |
| | Anti-Fyb | Reference method | 512 | 74 | 512 |
| | | Reference method contaminated | 512 | 74 | 512 |
| | | Dilution in the test card method contaminated | 512 | 77 | 512 |
| | Anti-S | Reference method | 32 | 42 | 32 |
| | | Reference method contaminated | 32 | 42 | 32 |
| | | Dilution in the test card method contaminated | 32 | 42 | 32 |
| | Anti-M | Reference method | 4 | 12 | 4 |
| | | Reference method contaminated | 4 | 15 | 4 |
| | | Dilution in the test card method contaminated | 4 | 15 | 4 |
| | Anti-C | Reference method | 2048 | 106 | 2048 |
| | | Reference method contaminated | 2048 | 106 | 2048 |
| | | Dilution in the test card method contaminated | 2048 | 106 | 2048 |
| | Anti-Kpb | Reference method | 1 | 5 | 1 |
| | | Reference method contaminated | 1 | 5 | 1 |
| | | Dilution in the test card method contaminated | 1 | 5 | 1 |
| Reverse grouping | Plasma A | Reference method | 8 | 31 | 8 |
| | | Dilution in the test card method | 8 | 31 | 8 |
| | Plasma A | Reference method | 16 | 45 | 32 |
| | | Dilution in the test card method | 16 | 45 | 32 |
| | Plasma A | Reference method | 2 | 17 | 4 |
| | | Dilution in the test card method | 2 | 17 | 4 |
| | Plasma O | Reference method | 64 | 71 | 128 |
| | | Dilution in the test card method | 64 | 69 | 128 |
| | Plasma O | Reference method | 16 | 47 | 32 |
| | | Dilution in the test card method | 16 | 47 | 32 |
| | Plasma O | Reference method | 4 | 25 | 4 |
| | | Dilution in the test card method | 4 | 25 | 4 |

The results in Table 1 show that mixing anti-serum within the incubation chamber (i.e., Dilution in the test card method) showed the same performance as performing the titration in separate test tubes (i.e., Reference method). The results also show that contaminating the incubation chamber with AHG due to, e.g., bad transport conditions, did not impact the performance of the gel once the cards were centrifuged prior to testing. Thus, the results shown in Table 1 illustrate no significant difference in titer, score, and endpoint between methods and that dilutions for determining an antibody titer can be performed within the incubation chambers of the gel test card without contaminating the sample with gel reagent.

Example 2—Generation of Calibration Curve

Figure 18A:
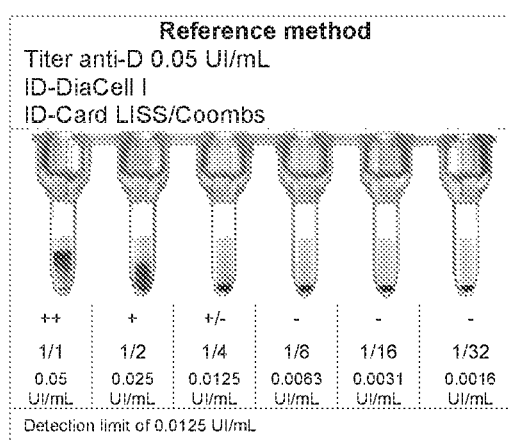
FIGS. 18A-18B show results from an experiment as described in Example 2 in which calibrator is diluted in tubes or directly in the test card.
Figure 18B:
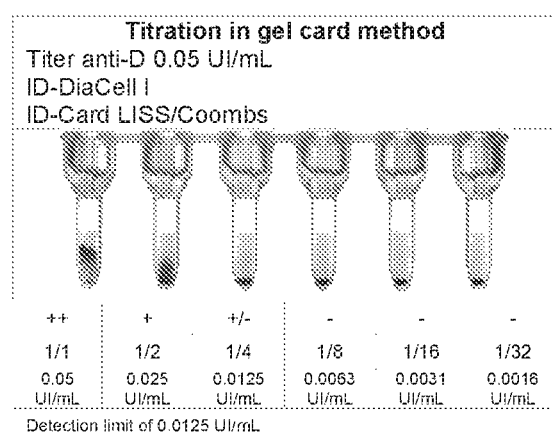

In this example, the feasibility of diluting a calibrator (or standard) directly in the test card to generate a calibration curve was tested.
Materials
1. ID-Card LISS/Coombs (DiaMed GmbH, Bio-Rad)
2. IH-QC1 (DiaMed GmbH, Bio-Rad) (The supernatant contains anti-D at 0.05 UI/mL. The anti-D 0.05 IU/ml is standardized against the World Health Organization 01/572 International Standard controlled by an external accredited reference laboratory by Continuous Flow Assay.)
3. ID-DiaCell I (DiaMed, GmbH, Bio-Rad)
4. ID-Titration Solution (DiaMed GmbH, Bio-Rad)
5. Dilution tubes—Hemolysis glass tubes, Ratiolab (Ref. 2600131)
Methods
1. Reference method for dilution—Used the same method as for Example 1 using the ID-Card LISS/Coombs. The IH-QC1 (anti-D 0.05 UI/mL) was the sample for dilution.
2. Dilution in the test card method—Used the same method as for Example 1 using the ID-Card LISS/Coombs. The IH-QC1 (anti-D 0.05 UI/mL) is the sample for dilution.
Results The results are shown in FIGS. 18A and 18B. Reaction grade and sample dilution are reported in the figures. Similar results were obtained for both methods, illustrating that the calibration curve can be generated by diluting a calibrator directly in the incubation chambers of the test card.

Example 3—Determination of Concentration of an Antigen

Figure 19A:
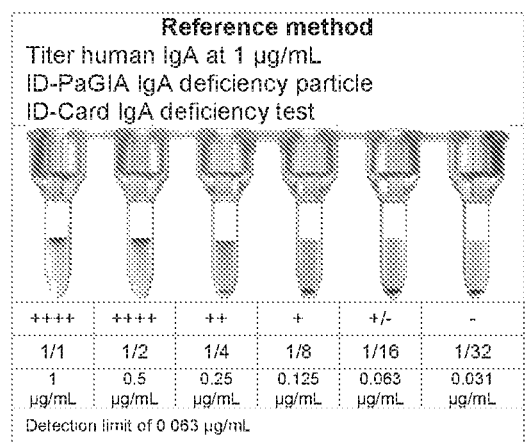
FIGS. 19A-19B show results from an experiment as described in Example 3 in which a concentration of an antigen (human IgA) is determined.
Figure 19B:
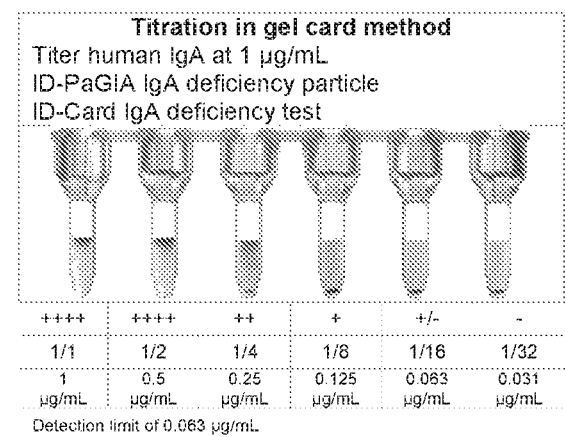

In this example, the feasibility of using coated particles to determine an antigen concentration was tested.
Materials
1. ID-Card IgA deficiency test (DiaMed GmbH, Bio-Rad)
2. ID-PaGIA IgA deficiency particle (DiaMed GmbH, Bio-Rad)
3. ChromoPure Human IgA (Jackson Immunoresearch) (4.8 mg/mL)
4. ID-Titration Solution (DiaMed GmbH, Bio-Rad) (Human IgA is diluted at 1 μg/mL in ID-Titration Solution. This sample can be considered as a calibrator as well.)
5. Dilution tubes—Hemolysis glass tubes, Ratiolab (Ref. 2600131)
Methods
1. Reference Method for Dilution
   a. Identified the suspension tubes according to the number of dilution steps to be performed, e.g. tube 1 (undiluted sample, 1/1), tube 2 (dilution 1/2), tube 3 (dilution 1/4).
   b. Dispensed 500 μl of ID-Titration Solution in each suspension tube except in tube 1 (undiluted).

c. Dispensed 500 µl of Human IgA at 1 µg/mL in tube 1 and microtube 2. Changed tips and mixed the content of tube 2 by pipetting up and down 4-5 times.
d. From this mix, removed 500 µl and dispensed it to tube 3. Changed tips and mixed the content of tube 3 by pipetting up and down 4-5 times.
e. Continued the same process for all dilutions using clean tips to mix and transfer to each dilution. From the final tube, removed 500 µl of diluted sample and saved it for use if further dilutions were required.
  Note that the volume used to perform the serial twofold dilution (here 500 µl) must be adapted to the sample volume availability as well as to the suspension tubes used.
f. Proceeded immediately to testing in ID-Card IgA deficiency test as follows:
  Identified ID-Card microtubes for the appropriate dilutions.
  Transferred 10 µl of each diluted sample, from the highest to the lowest dilution in each microtube, followed by 50 µl of ID-PaGIA IgA deficiency particles.
  Incubated 5 min at room temperature.
  Centrifuged 10 min the ID-Cards in the ID-Centrifuge.
  Read and recorded the reaction results.
2. Dilution in the Test Card Method
  a. Identified ID-Card IgA deficiency test microtubes for the appropriate dilutions.
  b. Dispensed 10 µl of ID-Titration Solution in each ID-Card microtubes with the exception of the first microtube (undiluted sample).
  c. Dispensed 10 µl of Human IgA at 1 µg/mL in ID-Card microtube 1 and 2. Changed tips and mixed the content of microtube 2 by pipetting up and down 4-5 times.
  d. From this mix, removed 10 µl and dispense in microtube 3. Changed tips and mixed the content of microtube 3 by pipetting up and down 4-5 times.
  e. Continued the same process for all dilutions using clean tips to mix and transferred to each dilution. From the final microtube, removed 10 µl of diluted sample.
  f. Immediately after dilution, added 50 µl of ID-PaGIA IgA deficiency particles to each microtube.
  g. Incubated 5 min at room temperature.
  h. Centrifuged 10 min the ID-Cards in the ID-Centrifuge.
  i. Read and recorded the reaction results.
Results Results are shown in FIGS. 19A and 19B. Reaction grade and sample dilution are reported in the figures. Similar results were obtained for both methods, illustrating that the antigen concentration can be determined by diluting antigen directly in the incubation chambers of the test card.

It is understood that the examples and embodiments described herein are for illustrative purposes only and that various modifications or changes in light thereof will be suggested to persons skilled in the art and are to be included within the spirit and purview of this application and scope of the appended claims. All patents, patent applications, internet sources, and other published reference materials cited in this specification are incorporated herein by reference in their entireties. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

The invention claimed is:

1. A method of determining a concentration of an analyte in a sample by in situ serial dilution, the method comprising:
  providing an immunodiagnostic test card, the test card comprising a substantially flat support that supports a plurality of vertically disposed microtubes, each microtube having an incubation chamber for receiving the sample and a reaction chamber comprising a separation matrix;
  adding a diluent to at least one of the incubation chambers;
  serially diluting the sample directly into each of the incubation chambers having diluent therein;
  adding a reagent to each of the incubation chambers having diluent and/or sample therein, wherein the reagent is capable of complexing with the analyte to form a reagent-analyte complex;
  exposing the mixture of sample and reagent to sedimentation by gravitation and/or centrifugation; and
  determining the concentration of the analyte by determining a highest dilution of the sample at which a reagent-analyte complex is detected on or within the separation matrix.

2. The method of claim 1, wherein the determining the concentration of the analyte step comprises determining a titer of an antibody and the titer is the highest dilution of the sample for which a reagent-antibody complex is observed corresponding to a reaction strength of "+".

3. The method of claim 2, further comprising determining an antibody endpoint and the antibody endpoint is the highest dilution of the sample having visible reagent-antibody complexes.

4. The method of claim 2, further comprises determining an antibody titer score and the antibody titer score is the sum of the score values assigned to each reaction.

5. The method of claim 2, wherein the antibody is directed against a red blood cell antigen.

6. The method of claim 1, wherein the determining the concentration of the analyte step comprises determining the concentration of an antigen.

7. The method of claim 1, wherein the separation matrix is a polyelectrolyte gel.

8. The method of claim 7, wherein the polyelectrolyte gel is dextran acrylamide.

9. The method of claim 1, wherein the reaction chamber further comprises a reticulation agent.

10. The method of claim 9, wherein the reticulation agent is a secondary antibody.

11. The method of claim 10, wherein the secondary antibody is anti-human globulin or anti-human IgA antibody.

12. The method of claim 1, wherein the serially diluting the sample step comprises serially diluting the sample directly into each of the incubation chambers in the same test card or between test cards.

13. The method of claim 1, wherein the reagent comprises a red blood cell or a coated particle having an antigen or antibody thereon.

14. The method of claim 1, wherein each microtube further comprises an air gap between the incubation chamber and the reaction chamber.

15. The method of claim 1, wherein each microtube further comprises a low density immiscible compound between the incubation chamber and the reaction chamber.

16. The method of claim 1, further comprising mixing the reagent and the sample after the step of adding the reagent to each of the incubation chambers having diluent and/or sample therein.

17. The method of claim 1, further comprising incubating the test card after the step of adding the reagent to each of the incubation chambers having diluent and/or sample therein.

18. The method of claim 1, wherein the serially diluting the sample step comprises:
   a) at least a two-fold serial dilution of the sample into each of the incubation chambers having diluent therein;
   b) less than a two-fold serial dilution of the sample into each of the incubation chambers having diluent therein; or
   c) a two-fold serial dilution of the sample into each of the incubation chambers having diluent therein.

19. The method of claim 1, wherein the sample is selected from the group consisting of serum, plasma, and a calibrator.

20. The method of claim 1, wherein the analyte is an antibody or an antigen.

* * * * *